United States Patent [19]

Cain

[11] Patent Number: 4,609,349
[45] Date of Patent: Sep. 2, 1986

[54] ACTIVE REMOVABLE ORTHODONTIC APPLIANCE AND METHOD OF STRAIGHTENING TEETH

[76] Inventor: Steve B. Cain, 407 NW. Briarcliff Extension, Kansas City, Mo. 64116

[21] Appl. No.: 653,367

[22] Filed: Sep. 24, 1984

[51] Int. Cl.$^4$ ............................................... A61C 3/00
[52] U.S. Cl. .......................................... 433/6; 433/7; 433/18
[58] Field of Search .......................... 433/6, 7, 18, 21

[56] References Cited

U.S. PATENT DOCUMENTS

| | | | |
|---|---|---|---|
| 2,266,860 | 12/1941 | Griesinger | 433/7 |
| 3,407,500 | 10/1968 | Kesling | 433/6 |
| 3,510,946 | 5/1970 | Kesling | 433/6 |
| 3,574,941 | 4/1971 | Ritter | 433/18 |
| 3,827,146 | 8/1974 | Wallshein | 433/7 |
| 4,054,996 | 10/1977 | Wallshein | 433/7 |
| 4,139,944 | 2/1979 | Bergersen | 433/6 |

Primary Examiner—John J. Wilson
Attorney, Agent, or Firm—Kokjer, Kircher, Bradley, Wharton, Bowman & Johnson

[57] ABSTRACT

A thermoplastic vacuum formed active dental retainer and method of straightening teeth. The retainer of the invention is made by first making a plaster or other suitable model of the teeth and then forming a plastic overlay by means of vacuum forming a thin clear plastic material over the model. Secured to the surface of the oral cavity portion of the overlay is a tubular member which may either serve itself as a tensioning member or mount a wire spring-like tensioning member. The tubular member and tensioning member are positioned in such a manner as to be in proper alignment with the tooth to be straightened. A number of bends in the tubular member and the tensioning member allow for exertion of a force over a relatively long distance thus increasing the amount of work any given size wire can perform over what could be accomplished with a straight wire of the same size. The overall thickness of the overlay and tensioning member may thus be kept to a minimum thereby allowing for a retainer which can accomplish corrections of prior art devices yet does not violate freeway space, provides for precise positioning of the tensioning member, provides absolute anchoring of the teeth that are to remain stationary, may be used to correct a single tooth or two or more teeth simultaneously, may be used on either the upper or lower teeth, and is more aesthetically pleasing.

12 Claims, 5 Drawing Figures

ACTIVE REMOVABLE ORTHODONTIC APPLIANCE AND METHOD OF STRAIGHTENING TEETH

This invention relates to orthodontic appliances and, more particularly, to a thermoplastic vacuum formed active removable appliance and a method of straightening teeth.

The primary objective of orthodontia is to produce normal occlusion of the teeth and facial harmony. Both mechanical appliances and elastic traction are employed for a period of time to allow for bone growth and muscle changes. A normal relationship of the teeth and jaws is desirable to give proper shape and expression to the mouth and face and aids in enunciation of words as well as permitting proper mastication of food.

Various types of tooth positioning appliances are known in the prior art. The most widely utilized technique for straightening teeth is the placement of wire braces which extend over the teeth often in combination with elastomeric tensioning devices. One or more teeth are moved by adjusting the wires which extend over the teeth being moved as well as adjacent teeth which serve as anchors.

It is also known in the prior art to utilize a "finishing" appliance to hold the teeth in place after movement while the root systems become permanently firm in the bone structure of the mouth. A typical prior art finishing device consists of a molded plastic insert which fits within the oral cavity between the teeth being straightened with one or more retaining wires extending from the plastic insert to engage the teeth. In some instances, slight movement of the teeth is achieved with a finishing device of the type described by incorporating a tensioning member into the plastic insert that seats in the oral cavity. Utilizing prior art constructions, however, it is necessary that the plastic overlay be relatively thick to accommodate the typical wire spring-like tensioning member which is imbedded in it. On the other hand, in order to keep the thickness of the plastic overlay to an acceptable dimension, it is necessary to utilize a relatively thin or small diameter tensioning member. This in turn limits the amount of force which can be applied to a tooth. Another disadvantage of utilizing a retainer to effect movement of a tooth is that it is not uncommon for undesired movement of some teeth to also occur. With most common forms of orthodontic appliances, the wires through which straightening forces are applied are subject to distortion as a result of accidental contact with objects placed in the mouth. This can result in the wire becoming ineffective or even applying an undesired force.

It is also known to utilize finishing appliances which form a substantially complete overlay of the teeth and are made of clear plastic. In some instances, these devices are of relatively thick construction which preclude complete occlusion of the teeth by occupying a portion of the "freeway" space which is the separation between the upper and lower occluding surfaces of the teeth when the teeth are in physiologic rest position.

Another type of clear plastic finishing appliance is a thermoplastic material which is formed from a relatively thin sheet to provide a complete overlay of the teeth and can thus be utilized to present a substantially "invisible" retainer. While a device of this type does have advantages in that it is more aesthetically pleasing and does not encroach on free-way space, the thickness of the material utilized must of necessity be so thin as not to accommodate the placement of a tensioning member within the sheet.

A variation on a conventional retainer is also shown and described in U.S. Pat. No. 4,054,996.

The present invention incorporates the advantages of a clear plastic overlay retainer that does not violate free-way space with active type retainers that have heretofore been utilized to accomplish relatively small tooth movement. The present invention provides an even better active removable orthodontic appliance and method which is superior to the prior art devices discussed above because it is not necessary to limit the size of the tensioning member to the thickness of the plastic overlay and, because of the unique construction, a relatively strong positioning force may be achieved utilizing a tensioning member of optimal size. Furthermore, the device of the present invention provides for an active removable orthodontic appliance wherein the tensioning members are protected from distortion by a plastic overlay.

It is therefore a primary object of the present invention to provide a method and device for straightening teeth whereby a substantially clear plastic overlay is all that is visible to the wearer and yet actual movement of one or more teeth to correct malocclusion is possible.

It is another primary objective of this invention to provide a method and appliance for straightening teeth which can accomplish many of the corrections heretofore limited to wire braces but with the aesthetic advantages of a clear plastic overlay that does not violate free-way space.

As a corollary to the foregoing objective, it is an aim of this invention to provide a method and appliance for straightening teeth which in many respects is comparable to conventional wire braces but is more aesthetically pleasing, more comfortable to the wearer and easier to clean than conventional braces.

Another one of the objects of my invention is to provide a method and appliance for straightening teeth wherein a relatively thin sheet-like plastic overlay of the teeth is utilized which does not violate free-way space and yet which incorporates a tensioning member that is not necessarily limited in size to the thickness of the overlay.

It is an important aim of the present invention to provide a method and appliance for straightening teeth which provides for protecting the tensioning members from distortion by the presence of a plastic overlay.

It is also one of the objectives of this invention to provide a method and appliance for straightening teeth which provides an active retainer having improved anchoring capabilities over devices of the prior art.

It is an object of the invention to provide a method and appliance for straightening teeth which meets the foregoing objects and which can be utilized on either upper or lower teeth.

Other objects of the invention will be made clear or become apparent from the following description and claims when read in light of the accompanying drawing, wherein:

Figure 1:
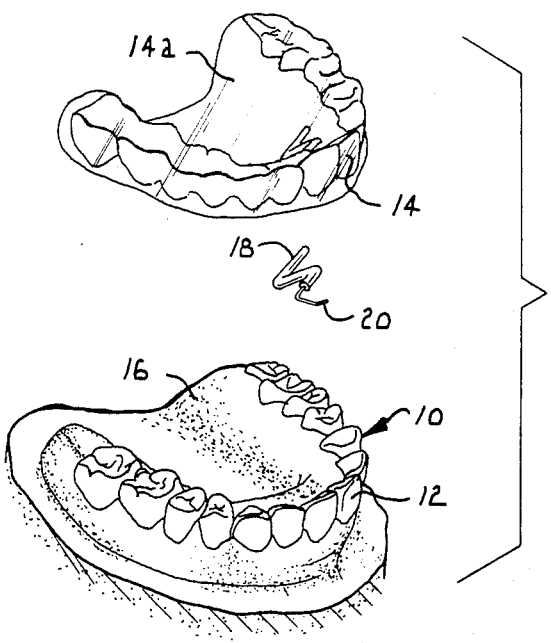
FIG. 1 is a perspective view of the upper teeth in combination with the device of the present invention, the upper teeth having been inverted for purposes of illustration.
Figure 2:
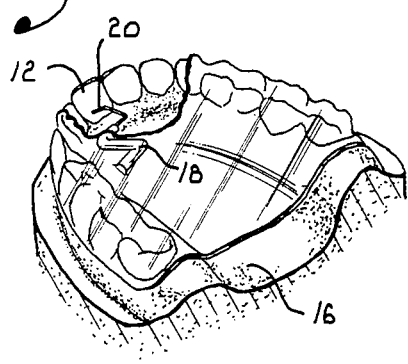
FIG. 2 is another perspective view with the device of the present invention in place in the oral cavity with a portion cut away for purposes of illustration.

Referring initially to FIG. 1, the teeth to be straightened are designated generally by the numeral 10 including one incisor 12 which is to be moved. Teeth 10 are representative of the upper human teeth although they have been shown in an inverted position for better illustration of the invention. It is to be understood that, while the present invention is explained herein with reference to a single tooth 12 being moved, the invention is applicable to moving two or more teeth in either or both of the upper and lower banks of teeth simultaneously.

Figure 3:
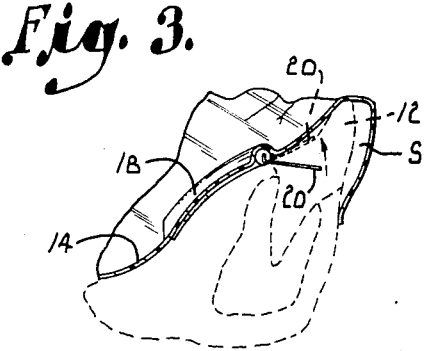
FIG. 3 is an enlarged vertical cross-sectional view taken through the teeth being straightened and illustrating the manner in which the tensioning member applies a force against a tooth to be moved.
Figure 4:
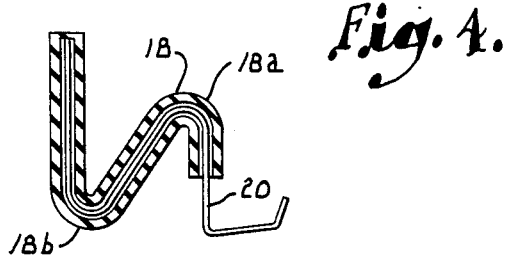
FIG. 4 is a horizontal cross-sectional view which illustrates in detail the tensioning member that forms a part of the device of the present invention.

An impression of teeth 10 is taken from which a plaster (or other suitable material) model is prepared utilizing conventional techniques well known to those skilled in the art. The model is then modified to provide for the necessary tooth movement that is desired. Next, a clear plastic overlay of teeth 10 is formed utilizing vacuum forming techniques which again are well known to those skilled in the art. A relatively thin clear sheet-like material which is initially flat is placed over the model of the teeth and then vacuum formed to present overlay 14 that conforms precisely to the configuration of teeth 10 to be anchored while providing a space "S" for the tooth (or teeth) to be moved. Space "S" is illustrated in FIG. 3. It is to be noted that overlay 14 includes a portion 14a bridging that portion of the oral cavity 16 lying between the teeth to be straightened. In the example illustrated in the drawing, the area 16 represents the roof of the mouth. In the case of lower teeth, the overlay 14 would cover the hard tissue only. It is important to note that the sheet of plastic material from which overlay 14 is formed is of a thickness which does not violate the "free-way" space during full occlusion of the upper and lower teeth.

Secured to the surface of overlay 14 and in particular to the portion 14a on the side of the latter which contacts the tissue adjacent tooth 12 within the oral cavity 16 is an elongated tubular member 18 which is affixed to the surface of the overlay in a non-linear configuration preferably with two bends 18a and 18b of 60°-90° each. The securing of tubular member 18 to overlay 14 is normally accomplished by adhesively securing the tube to the plaster model and then forming the overlay over the tube simultaneously with conforming it to the shape of the teeth. Tubular member 18 may itself serve as a tensioning member as will be more fully explained hereinafter or in the preferred embodiment serve to mount an elongated wire spring-like tensioning member 20. It is to be understood that, in the preferred embodiment of the invention, the inside diameter of tubular member 18 is enough larger than the outside diameter of tensioning member 20 so as to accommodate movement of the latter relative to the tubular member. Alternatively, tensioning member 18 may be dip coated in a compatable coating to form a tubular member that tightly fits over tensioning member 20. It is also within the scope of the present invention to secure tubular member 18 to overlay 14 after the overlay has been formed over the model of the teeth by an adhesive, ultrasonic welding, or other suitable means.

Tensioning member 20 is, of course, placed on the surface of overlay 14 to align with the tooth 12 to be straightened. The appropriate size and length of spring tensioning member 20 is selected to apply the force indicated to achieve the desired movement. It is to be noted that the relatively long length of spring wire 20 together with the presence of bends at the corresponding bends in tube 18 cause the spring memory of the wire to exert a force over a relatively long distance thus increasing the effective force that is applied at tooth 12 relative to what could be achieved with a shorter wire. This is possible because of the freedom of movement between member 20 and tubular member 18. Also, the tubular member, being constructed of resilient material, will enhance the spring force achieved through tensioning member 20. Because the effectiveness of the force applied through member 20 is increased by applying the force over a greater distance than would be possible with a linear arrangement, the size and spring force of the member 20 may be reduced over what would otherwise be required. This in turn allows the overall thickness of the overlay in combination with the tensioning member to be kept to a minimum while still providing a tensioning member capable of providing the required force.

After the tensioning member is inserted inside of tube 18 and properly positioned for alignment with tooth 12, the overlay 14 is placed inside of the mouth of the wearer to cause the tensioning member 20 to engage tooth 12. FIG. 3 illustrates the position that the tensioning member 20 would assume as a result of its own spring memory but for being placed against tooth 12. This position is illustrated in broken lines with the solid line position of member 12 showing how it is placed in contact with the tooth. Tensioning member 20 exerts a force against tooth 12 to move it into the space "S" while overlay 14 holds the remaining teeth stationary. The construction of overlay 14 makes it much more effective in providing an absolute anchor than the prior art retainers which employ wires.

As indicated above, in some applications it may be desirable to utilize tube 18 as the tensioning member. This would be in instances where a relatively light force is required and such force can be obtained from a resilient tubular member. In such constructions, the spring wire tensioning member would be deleted and instead the tubular member 18 of resilient material would be placed so as to contact tooth 12 to be moved.

Figure 5:
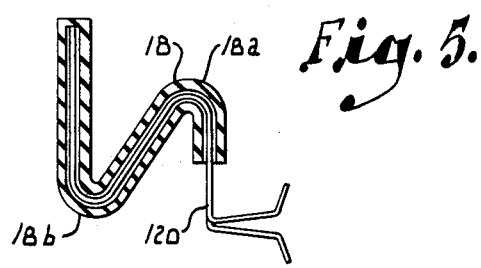
FIG. 5 is a cross-sectional view, similar to FIG. 4, of an alternative embodiment of the invention.

Manifestly, it will be desirable in many instances to incorporate more than one tensioning member into the surface of overlay 14 so as to move two or more teeth simultaneously. In other applications, it may be possible to accomplish movement of a plurality of teeth utilizing a single tensioning member having a plurality of tooth contacting surfaces. This alternative embodiment is illustrated in FIG. 5 with the tensioning member being designated by the numeral 120. Another alternative construction is to employ multiple tensioning members 20 in a single resilient tube 18.

It is to be understood that both overlay 14 and resilient tube 18 should be constructed from an inert FDA approved human safe plastic, serveral of which are readily available.

I claim:

1. A method of straightening teeth comprising: forming a thin sheet-like plastic overlay of the teeth, including the tooth to be straightened and at least some of the teeth on either side of said tooth, said overlay being of a thickness so as not to violate the freeway space between upper and lower occluding teeth surfaces;

providing a spring like tensioning member having the ability to undergo deformation while retaining its spring memory;

providing a resilient tubular member for at least partially encasing said tensioning member;

placing said tensioning member inside of said tubular member, a portion of the tensioning member being positioned for engagement with said tooth to be straightened;

securing said tubular member and said tensioning member to the surface of said overlay in a manner to cause one or more bends in both the tubular member and the tensioning member; and placing said overlay inside of the mouth of a wearer with said portion of said tensioning member engaging said tooth to be straightened, whereby said tensioning member effects movement of said tooth to be straightened while said overlay provides an anchor for holding the remaining teeth stationary.

2. A method as set forth in claim 1, wherein said forming step comprises forming said sheet-like plastic overlay of substantially transparent material.

3. A method as set forth in claim 1, wherein said securing step comprises securing said tube to the side of said sheet which contacts the tissue within the oral cavity.

4. A method as set forth in claim 1, wherein said tensioning member is characterized by a size sufficiently smaller than said tube to accommodate movement of said member relative to said tube.

5. A method as set forth in claim 1, wherein said steps of providing a tubular member and placing said tensioning member inside of the tubular member include coating said tensioning member with a material for forming said tubular member in tight fitting relationship to the tensioning member.

6. An orthodontic appliance for straightening the teeth of a wearer comprising:

a thin sheet-like plastic overlay for covering the teeth including a tooth to be straightened and at least some of the teeth on either side of said tooth, said overlay extending over at least a portion of the tissue adjacent said teeth and being of a thickness so as not to violate the freeway space between upper and lower occluding teeth surfaces;

a spring like tensioning member having the ability to undergo deformation while retaining its spring memory; and a resilient tubular member partially encasing said tensioning member, said tensioning member and said tubular member being secured to the surface of said overlay in a manner to cause one or more bends in both the tubular member and the tensioning member with a portion of said tensioning member being positioned for engagement with a tooth to be straightened, whereby when said appliance is placed in the mouth with said tensioning member engaging said tooth to be straightened this tooth is moved while said overlay holds the remaining teeth in a stationary position.

7. An orthodontic appliance as set forth in claim 6, wherein said tubular member comprises a hollow elongated tube, and said tensioning member is disposed inside of said tube in non-rigid relationship thereto.

8. An orthodontic appliance as set forth in claim 7, wherein said tensioning member is characterized by a size sufficiently smaller than said tube to accommodate movement of said member relative to said tube.

9. An orthodontic appliance as set forth in claim 7, wherein said tube is secured to the side of said sheet which contacts said tissue.

10. An orthodontic appliance as set forth in claim 7, wherein said overlay is substantially transparent.

11. An orthodontic appliance as set forth in claim 10, wherein said tensioning member comprises a wire having spring properties.

12. An orthodontic appliance as set forth in claim 6, wherein said tensioning member is dip coated in an inert nontoxic plastic to form said tubular member.

* * * * *